US010709776B2

(12) United States Patent
Oswald et al.

(10) Patent No.: US 10,709,776 B2
(45) Date of Patent: Jul. 14, 2020

(54) METHOD FOR PRODUCING OUTER MEMBRANE VESICLES

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); INSTITUT NATIONAL DE LA RECHERCHE AGRONOMIQUE (INRA), Paris (FR); UNIVERSITÉ PAUL SABATIER TOULOUSE III, Toulouse (FR); CENTRE HOSPITALIER UNIVERSITAIRE DE TOULOUSE, Toulouse (FR)

(72) Inventors: Eric Oswald, Toulouse (FR); Patricia Martin, Toulouse (FR); Kazunori Murase, Miyazaki (JP)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); INSTITUT NATIONAL DE RECHERCHE POUR L'AGRICULTURE, L'ALIMENTATION ET L'ENVIRONNEMENT, Paris (FR); UNIVERSITÉ PAUL SABATIER TOULOUSE III, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 53 days.

(21) Appl. No.: 15/302,279

(22) PCT Filed: Apr. 7, 2015

(86) PCT No.: PCT/EP2015/057500
§ 371 (c)(1),
(2) Date: Oct. 6, 2016

(87) PCT Pub. No.: WO2015/155178
PCT Pub. Date: Oct. 15, 2015

(65) Prior Publication Data
US 2017/0112913 A1    Apr. 27, 2017

(30) Foreign Application Priority Data
Apr. 7, 2014  (EP) .................................... 14305508

(51) Int. Cl.
| A61K 39/108 | (2006.01) |
| C12N 1/20 | (2006.01) |
| A61K 39/00 | (2006.01) |
| C12N 1/06 | (2006.01) |
| C07K 14/245 | (2006.01) |
| C12N 1/02 | (2006.01) |
| C12Q 1/18 | (2006.01) |

(52) U.S. Cl.
CPC ........ *A61K 39/0258* (2013.01); *C07K 14/245* (2013.01); *C12N 1/02* (2013.01); *C12N 1/06* (2013.01); *C12N 1/066* (2013.01); *C12N 1/20* (2013.01); *C12Q 1/18* (2013.01); *A61K 2039/52* (2013.01); *A61K 2039/555* (2013.01); *G01N 2500/04* (2013.01)

(58) Field of Classification Search
None
See application file for complete search history.

(56) References Cited

U.S. PATENT DOCUMENTS

| 2017/0112913 A1* | 4/2017 | Oswald .............. A61K 39/0258 |
| 2017/0130227 A1* | 5/2017 | Lizasoain Hernandez .................. A61K 31/7088 |
| 2018/0207255 A1* | 7/2018 | Grandi .................. A61K 39/02 |

FOREIGN PATENT DOCUMENTS

| EP | 3129462 A1 * | 2/2017 | |
| WO | 2008/147816 A2 | 12/2008 | |
| WO | 2012/097185 A2 | 7/2012 | |
| WO | 2014/044728 A1 | 3/2014 | |
| WO | WO-2015144691 A1 * | 10/2015 | ........... A61K 39/085 |
| WO | WO-2015155178 A1 * | 10/2015 | ........... C07K 14/245 |

OTHER PUBLICATIONS

Murase et al, HlyF Produced by Extraintestinal Pathogenic *Escherichia coli* Is a Virulence factor That regulates Outer Membrane Vesicle Biogenesis. Journal of Infectious Diseases, Mar. 1, 2016, 213:856-865. published online Oct. 22, 2015. (Year: 2016).*
Chen et al, Delivery of foreign antigens by engineered outer membrane vesicle vaccines. PNAS, Feb. 16, 2010, 107/7:3099-3104. (Year: 2010).*
van de Waterbeemd et al, Improved OMV vaccine against Neisseria meningitidis using genetically engineered strains and a detergent-free purification process. Vaccine 2010, 28:4810-4816. (Year: 2010).*
Henry et al, Improved methods for producing outer membrane vesicles in Gram-negative bacteria. Research in Microbiology, 2004, 155:437-446. (Year: 2004).*
Collins Brenda S: "Gram-negative outer membrane vesicles in vaccine development", Discovery Medicine, US, vol. 12, No. 62, pp. 7-15, Jul. 2, 2011.
Chloe Lemaitre et al: "Transcriptional analysis of the *Escherichia coli* CoIV-1a plasmid pS88 during growth in human serum and urine", BMC Microbiology, Biomed Central Ltd, GB, vol. 12, No. 1, p. 6, Jun. 21, 2012.
Morales C et al: "Detection of a novel virulence gene and a *Salmonella* virulence homologue among *Escherichia coli* isolated from broiler chickens", Foodborne Pathogens and Disease, Mary Ann Liebert, Inc. Publishers, US, vol. 1, No. 3, abstract Oct. 4, 2014.
Martin P et al: "Role for hemolysin F in the virulence of *Escherichia coli*", Abstracts of the 114th General Meeting, American Society for Microbiology, p. 1, May 17, 2014.

* cited by examiner

*Primary Examiner* — Nita M. Minnifield
(74) *Attorney, Agent, or Firm* — W&C IP

(57) ABSTRACT

The present invention relates to ex vivo method for producing outer membrane vesicles (OMVs) by expression or overexpression of the hemolysin F gene (hlyF) in gram-negative bacterium.

7 Claims, 4 Drawing Sheets

Figure 1:
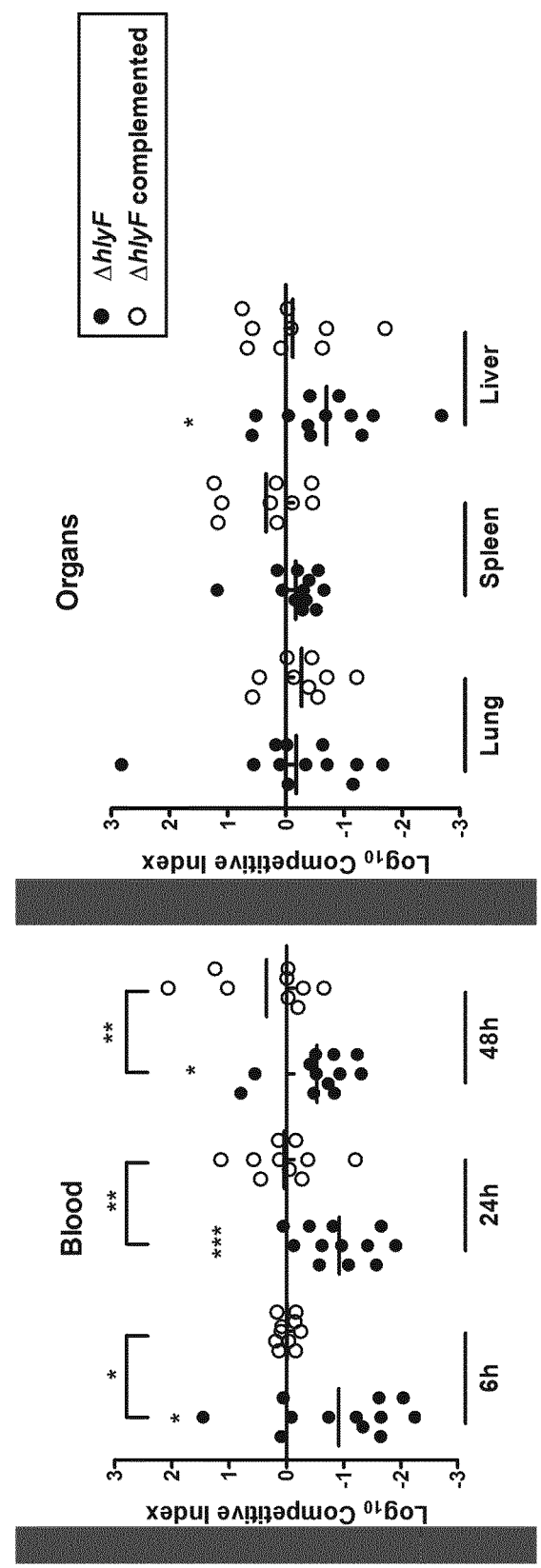

Specification includes a Sequence Listing.

METHOD FOR PRODUCING OUTER MEMBRANE VESICLES

FIELD OF THE INVENTION

The present invention relates to a method for producing outer membrane vesicles (OMVs) by expression or overexpression of the hemolysin F gene (hlyF) in gram-negative bacterium.

BACKGROUND OF THE INVENTION

Extra-intestinal pathogenic *Escherichia coli* (ExPEC) belong to the normal intestinal microbiota, but can cause pathologies such as urinary tract infection, newborn meningitis and sepsis in humans, or colibacillosis in poultry. Their pathogenic potential can be attributed to the expression of virulence and fitness-associated factors that are required for the establishment of the infection. Important virulence mechanisms involve adhesion, invasion, subversion of host defenses, signaling and direct interference with host cellular functions via toxins and other secreted effectors [Dobrindt U et al., 2008].

Avian pathogenic *E. coli* (APEC), a subgroup of ExPEC, cause extra-intestinal diseases in chickens known as colibacillosis, which are costly for the poultry industry as they significantly reduce production. Attempts to control colibacillosis through vaccination have only provided partial success. Therefore, it is crucial to identify APEC factors involved in disease and to decipher the molecular mechanism resulting in the establishment of an infection.

ColV plasmids have been strongly associated with APEC, but also to neonatal meningitis-associated *E. coli* (NMEC), which is another pathotype of ExPEC causing human neonatal meningitis [Peigne C et al., 2009]. ColV plasmids encode genes involved in the synthesis of bacteriocins, including colicin V, iron acquisition and transport mechanisms, avian-like hemolysins, outer membrane proteins and adhesins. These plasmids have been shown to play an important role in the virulence of ExPEC [Skyberg J A et al., 2006]. However, the contribution of individual genes harbored by the ColV plasmids to virulence remains to be elucidated.

Gene hlyF is one of the genes exhibited on ColV plasmids and is widely used as an epidemiological marker for APEC [Ahmed A M et al., 2013] and NMEC [Kaczmarek A et al., 2012]. Although an hemolysin function has been attributed to HlyF, little is known about the exact contribution of HlyF to the virulence of the strain. In a model of infection of the chick embryo, the transcription of the hlyF gene was shown to be strongly up-regulated, suggesting that HlyF could be involved in the establishment of avian extra-intestinal infection. However, hlyF was shown not to be up-regulated in human serum or in urine. Therefore, the precise role of HlyF in virulence of APEC and NMEC remains to be clarified.

SUMMARY OF THE INVENTION

Here, the inventors evidence that hlyF is involved in the production of outer membrane vesicles (OMVs). The induction of OMVs by HlyF could be useful to the delivery of antigen and thus to induction of vaccine response against said antigen.

Thus, the present invention relates to a method for producing outer membrane vesicles (OMVs) by expression or overexpression of the hemolysin F gene (hlyF) in gram-negative bacterium.

DETAILED DESCRIPTION OF THE INVENTION

A first aspect of the invention relates to a method for producing outer membrane vesicles (OMVs) by expression or overexpression of the hemolysin F gene (hlyF) in gram-negative bacterium.

In a particular embodiment, the invention relates to an ex-vivo or an in-vitro method for producing outer membrane vesicles (OMVs) by expression or overexpression of the hemolysin F gene (hlyF) in gram-negative bacterium.

As used herein the term "gene hlyF" denotes a gene which encodes a protein that was attributed a putative hemolysin function and which is expressed by certain strains of the Enterobacteriaceae family. An exemplary sequence for the gene hlyF is deposited in GenBank: AF155222.1. For example, HlyF gene is located on the pS88 plasmid from strain S88 (Accession number CAQ87216).

According to the invention, hlyF gene may be expressed or overexpressed by different means.

For example, in one embodiment, endogenous hemolysin F gene expressed by the bacterium (notably in certain strains of the Enterobacteriaceae family) may be overexpressed. In this case, bacterial genome may be modified to obtain an overexpression of the hemolysin F gene. For example, natural promoter of the hemolysin F gene may be modified to obtain an overexpression of this gene.

In another embodiment, the medium used to cultivate the bacterium may be modified to induce an expression or an overexpression of the hemolysin F gene. For example, a depletion of iron should be done to induce this overexpression.

In still another embodiment, the bacterium may be transform with hlyF gene. For example, the bacterium may be transform with a plasmid which expresses the hlyF gene.

Thus, according to the invention, the method for producing OMVs by expression or overexpression of the hemolysin F gene (hlyF) in gram-negative bacterium comprises the following steps:
 a) transform the bacterium with the hlyF gene and/or overexpress the endogenous hlyF gene of the bacterium;
 b) cultivate the bacterium in an appropriate medium
 c) centrifugate the culture;
 d) filtrate the supernatant;
 e) centrifugate the obtained supernatant.

As used herein the term OMVs for "Outer Membrane Vesicles" denotes released spheres of outer membrane with periplasmic content that contain biologically active molecules (toxins, proteins, DNA) produced from the outer membrane of Gram negative bacteria. These vesicles are often involved in pathogenic processes since they contribute to the long-distance delivery of bacterial virulence factors, promote inflammation and stimulate host immune response. OMVs formed by bacteria can also mediate intercellular exchange events including cell-cell signalling, protein and DNA exchange (see for example Berleman J et al., 2013).

OMVs obtained by the method of the invention may be used for vaccine purpose and thus express specific antigens to induce vaccine response against these antigens.

As used herein the term "antigen" refers to a molecule which is capable of being recognized by the immune system and/or being capable of inducing a humoral immune response and/or cellular immune response leading to the activation of B- and/or T-lymphocytes. An antigen can have one or more epitopes or antigenic sites (B- and T-epitopes).

According to the invention, OMVs contain at their surface (e.g. at their membranes) antigens which are specific of the bacterium used to produce the OMVs. In this way, OMVs may be directly used for a vaccine purpose. In function of the bacterium used, OMVs obtained by the method of the invention may induce a vaccine response against the antigen expressed at its surface. For example, to obtain a vaccine response against ExPEC, APEC or NMEC, the antigens FyuA, IroN, ChuA, IreA, Iha, and/or Usp may be used (see for example Wieser A et al., 2010).

In a particular embodiment, the antigen used may be the protein FyuA, the receptor for the yersiniabactin siderophore.

Thus, in one embodiment, the invention also relates to a method for producing outer membrane vesicles (OMVs) in gram-negative bacterium by expression or overexpression of the hemolysin F gene (hlyF) and by expression or overexpression of an antigen gene of the bacterium.

According to the invention, OMVs may also contain others antigens which are not specific of the bacterium used to produce the OMVs. In this way, OMVs is used as carrier of heterologous antigens and these antigens are express at the surface of the OMVs (e.g. at their membranes). In function of the heterologous antigen used, OMVs obtained by the method of the invention will induce a vaccine response against this antigen and not again the bacterium used to obtain the OMVs. In this case, OMVs will not express antigens specific of the bacterium and no vaccine response against this bacterium will be induced.

In another embodiment, the invention also relates to an ex vivo method for producing outer membrane vesicles (OMVs) vaccine by expression or overexpression of the hemolysin F gene (hlyF) and by expression or overexpression of an heterologous antigen gene in gram-negative bacterium.

In a particular embodiment, the invention also relates to an ex vivo method for producing OMVs by expression or overexpression of the hemolysin F gene (hlyF) in gram-negative bacterium comprising the following steps:
a) transform the bacterium with the hlyF gene or overexpress the endogenous hlyF gene of the bacterium;
b) transform the bacterium with an heterologous antigen gene;
c) cultivate the bacterium in an appropriate medium
d) centrifugate the culture;
e) filtrate the supernatant;
f) centrifugate the obtained supernatant.

At last, according to the invention, OMVs may express antigens specific of the bacterium used to obtain the OMVs but also heterologous antigens which are not specific of the bacterium used. In this way, all antigens are expressed at the surface of the OMVs (e.g. at their membranes). In function of the bacterium used and in function of the heterologous antigen, OMVs obtained by the method of the invention will induce a vaccine response against all antigens. In this case, divalent OMVs are obtained.

According to the invention, several specific antigens and several heterologous antigens may be used to obtain the appropriate vaccine response. In this case, multivalent OMVs are obtained.

In one embodiment, when an heterologous antigen is used, said antigen gene may be selected form genes from *Neisseria meningitidis* or *Neisseria meningitidis* serogroup A. In another embodiment, the antigen gene may genes encoding for the proteins PorA (P1.9 and P1.20), PorB (P3.4 and P3.21) and Opc form *Neisseria meningitidis*.

In a particular embodiment, the heterologous antigen may be a "Tumor associated antigen". As used herein, the term "tumor associated antigen" refers to an antigen that is characteristic of a tumor tissue. An example of a tumor associated antigen expressed by a tumor tissue may be the antigen prostatic acid phosphatise (see WO 2004026238) or MART peptide T (melanoma antigen).

According to the invention the antigen gene may also contain a signal sequence which allows the expression of the protein encoding by the gene in the membrane of the OMVs. Particularly, the signal sequence can be the signal sequence of FyuA (MKMTRLYPLALGGLLLPAIANA, SEQ ID NO:1), the signal sequence of OmpC (outer-membrane protein C) (MKVKVLSLLVPALLVAGAANA, SEQ ID NO:2), the signal sequence of PelB (pectate lyase B) (MKYLLPTAAAGLLLLAAQPAMA, SEQ ID NO:3), the signal sequence of OmpA (outer-membrane protein A) (MKKTAIAIAVALAGFATVAQA, SEQ ID NO:4), the signal sequence of StII (heat-stable enterotoxin 2) (MKKNIAFL-LASMFVFSIATNAYA, SEQ ID NO:5), the signal sequence of Endoxylanase (MFKFKKKFLVGLTAAFMSISMF-SATASA, SEQ ID NO:6), the signal sequence of PhoA (alkaline phosphatase) (MKQSTIALALLPLLFTPVTKA, SEQ ID NO:7), the signal sequence of OmpF (outer-membrane protein F) (MMKRNILAVIVPALLVAGTANA, SEQ ID NO:8), the signal sequence of PhoE (outer-membrane pore protein E) (MKKSTLALVVMGIVASASVQA, SEQ ID NO:9), the signal sequence of MalE (maltose-binding protein) (MKIKTGARILALSALTTMMFSASALA, SEQ ID NO:10), the signal sequence of Lpp (murein lipoprotein) (MKATKLVLGAVILGSTLLAG, SEQ ID NO:11), the signal sequence of LamB (X receptor protein) (MMITLRKL-PLAVAVAAGVMSAQAMA, SEQ ID NO:12), the signal sequence of OmpT (protease VII) (MRAKLLGIVLTTPI-AISSFA, SEQ ID NO:13) or the signal sequence of LTB (heat-labile enterotoxin subunit B) (MNKVKCYV-LFTALLSSLYAHG, SEQ ID NO:14).

An antigen (especially an heterologous antigen) can be prepared using a variety of methods well known in the art. A gene encoding any immunogenic polypeptide can be isolated and cloned, for example, in bacterial, yeast, insect, reptile or mammalian cells using recombinant methods well known in the art and described, for example in Sambrook et al., Molecular cloning: A Laboratory Manual, Cold Spring Harbor Laboratory, New York (1992) and in Ansubel et al., Current Protocols in Molecular Biology, John Wiley and Sons, Baltimore, Md. (1998). A number of genes encoding surface antigens from viral, bacterial and protozoan pathogens have been successfully cloned, expressed and used as antigens for vaccine development. For example, the major surface antigen of hepatitis B virus, HbsAg, the P subunit of choleratoxin, the enterotoxin of *E. coli*, the circumsporozoite protein of the malaria parasite, and a glycoprotein membrane antigen from Epstein-Barr virus, as well as tumor cell antigens, have been expressed in various well known vector/host systems, purified and used in vaccines.

A pathologically aberrant cell may also be used in a vaccine composition according to the invention can be obtained from any source such as one or more individuals having a pathological condition or ex vivo or in vitro cultured cells obtained from one or more such individuals, including a specific individual to be treated with the resulting vaccine.

In a particular embodiment, the transformation of the bacterium with the heterologous antigen gene can be made using a plasmid or not. The term "using a plasmid" denotes the fact that the heterologous antigen gene is expressed by a plasmid which is inserted into the bacterium cytoplasm. Alternatively, the hlyF gene can be integrated into the bacterial chromosome, in a neutral or silent location, under the control of an inducible promoter.

In a particular embodiment, the bacteria plasmid is pGEX-6P-1 or pSA10 (see for example Schlosser-Silverman E et al., 2000).

In one embodiment, the gram-negative bacterium is an Enterobacteriaceae or a *Pseudomonas*.

As used herein, the term "Enterobacteriaceae" denotes a large family of Gram-negative bacteria that includes, along with many harmless symbionts, many of the more familiar pathogens, such as *Salmonella, Escherichia coli, Yersinia pestis, Klebsiella* and *Shigella*. This family is the only representative in the order Enterobacteriales of the class Gammaproteobacteria in the phylum Proteobacteria. Bacteria classified as members of Enterobacteriaceae may be *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Cronobacter, Dickeya, Edwardsiella, Enterobacter, Enterobacter aerogenes, Erwinia,* e.g. *Erwinia amylovora, Erwinia tracheiphila, Erwinia carotovora,* etc., *Escherichia,* e.g. *Escherichia coli, Ewingella, Grimontella, Hafnia, Klebsiella,* e.g. *Klebsiella pneumonia, Kluyvera, Leclercia, Leminorella, Moellerella, Morganella, Obesumbacterium, Pantoea, Pectobacterium* see *Erwinia, Candidatus Phlomobacter, Photorhabdus,* e.g. *Photorhabdus luminescens, Plesiomonas,* e.g. *Plesiomonas shigelloides, Pragia, Proteus,* e.g. *Proteus vulgaris, Providencia, Rahnella, Raoultella, Salmonella, Samsonia, Serratia,* e.g. *Serratia marcescens, Shigella, Sodalis, Tatumella, Trabulsiella, Wigglesworthia, Xenorhabdus, Yersinia,* e.g. *Yersinia pestis* and *Yokenella.*

In one embodiment, the Enterobacteriaceae is an *Escherichia coli*, an extra-intestinal pathogenic *E. coli* (ExPEC) like the avian pathogenic *E. coli* (APEC) or the neonatal meningitis-associated *E. coli* (NMEC).

In another embodiment, the *Escherichia coli* used in the method according to the invention is the IHE3034 strain, the SP15 strain, the K12 strain, the MG1655 strain and the BL21 strain.

As used herein, the term "*Pseudomonas*" denotes a large family of Gram-negative bacteria that includes, *P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, P. agarici, P. asplenii, P. aurantiaca, P. aureofaciens, P. chlororaphis, P. corrugate, P. fragi, P. lundensis, P. taetrolens, P. Antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridian, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. oryzihabitans, P. parafulva, P. plecoglossicida, P. putida, P. balearica, P. luteola, P. stutzeri, P. amygdale, P. avellanae, P. caricapapayae, P. cichorii, P. coronafaciens, P. ficuserectae, P. helianthi, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophila, P. psychrotolerans, P. rathonis, P. reptilivora, P. resiniphila, P. rhizosphaerae, P. rubescens, P. salomonii, P. segitis, P. septic, P. simiae, P. suis, P. thermotolerans, P. toyotomiensis, P. tremae, P. trivialis, P. turbinellae, P. tuticorinensis, P. umsongensis, P. vancouverensis, P. vranovensis* and *P. xanthomarina.*

In one embodiment, the hlyF gene can be also expressed directly into the bacterium DNA or into a plasmid in the cytoplasm of the bacterium.

In a particular embodiment, the transformation of the bacterium with the hlyF gene can be made using a plasmid. The term "using a plasmid" denotes the fact that the hlyF gene is expressed by a plasmid which is inserted into the bacterium cytoplasm.

In a particular embodiment, the bacteria plasmid is pGEX-6P-1.

In a particular embodiment, the hlyF gene expression is controlled by a promoter which induced a strong expression of the hlyF gene. In one embodiment, the promoter used is the IPTG inducible promoter pTAC or the arabinose inducible promoter pBAD.

In one embodiment, the medium used according to the methods of the invention may contain an antibiotic selected in the list but not limited to ampicillin, nalidixic acid, gentamicin, kanamycin, trimethoprim.

In a particular embodiment, the medium used is the LB (Luria-Bertani) medium.

Several steps of centrifugation are added. To remove the OMVs from bacteria the medium can be centrifuged with forces like 5,000 to 20,000 r.p.m for about 5 min to 2 hours and particularly 7,000 r.p.m for 10 min. To pellet the OMVs, the medium can be centrifuged with forces like 100,000 to 200,000 r.p.m for about 1 hour min to 4 hours and particularly 150,000 r.p.m for 3 hours min.

According to the invention, a step of suspension (step g)) can be added to obtain the OMVs in an appropriate medium. For example, the OMVs can be suspended in Tris-HCL.

According to the invention, a step of detoxification of the OMVs may be added. This step may be useful for example to deplete the OMVs from LPS and others toxic particles.

The invention also relates to the use of the hemolysine F gene (hlyF) for the production of outer membrane vesicles (OMVs) in gram-negative bacterium.

OMVs Obtained by the Method of the Invention

In another object, the invention relates to OMVs obtainable by the methods as above described.

According to the examples, OMVs were isolated from *E. coli* and were observed by transmission electron microscopy (TEM). A time-course analysis of the production of OMVs was performed and revealed that the amount of OMVs produced was gradually increased with cultivation time. The amount of OMVs produced was higher upon hlyF overexpression, at 24 h cultivation.

The proteins located in the OMVs were extracted, run on a SDS-PAGE gel and quantified. This revealed that the amount of total proteins significantly increased in *E. coli* when hlyF was overexpressed. Moreover, the increase of total proteins was amplified upon induction of the expression of the hlyF gene with IPTG.

Vaccine Composition

In a further object of the invention, the OMVs obtainable by the method described may be used for the preparation of a vaccine composition.

Hence, the present invention also provides a vaccine composition comprising the OMVs according to the invention.

According to the invention, the vaccine composition may comprise OMVs with specific antigens of the bacterium used to produce the OMVS and/or may comprise heterologous antigens.

A "vaccine composition", once it has been administered to a subject or an animal, elicits a protective immune response against said one or more antigen(s) that is (are) comprised herein. Accordingly, the vaccine composition of the invention, once it has been administered to the subject or the animal, induces a protective immune response against, for example, a microorganism, or to efficaciously protect the subject or the animal against infection.

The vaccine composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e. g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein, the term "adjuvant" refers to a substance that enhances, augments or potentiates the host's immune response to an antigen, e.g., an antigen that is part of a vaccine. Non-limiting examples of some commonly used vaccine adjuvants include insoluble aluminum compounds, calcium phosphate, liposomes, Virosomes™, ISCOMS®, microparticles (e.g., PLG), emulsions (e.g., MF59, Montanides), virus-like particles & viral vectors. PolyICLC (a synthetic complex of carboxymethylcellulose, polyinosinic-polycytidylic acid, and poly-L-lysine double-stranded RNA), which is a TLR3 agonist, is used as an adjuvant in the present invention. It will be understood that other TLR agonists may also be used (e.g. TLR4 agonists, TLR5 agonists, TLR7 agonists, TLR9 agonists), or any combinations or modifications thereof.

Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-[gamma], IL-2 and IL-12) or synthetic IFN-[gamma] inducers such as poly I:C can be used in combination with adjuvants described herein.

Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

As used herein, the term "TLR4 agonist" denotes a compound or a molecule which bind the Toll-like receptor 4 and active it. According to the invention, a TLR4 agonist may be selected from the group consisting of Ethanol, Morphine-3-glucuronide, Morphine, Oxycodone, Levorphanol, Pethidine, Glucuronoxylomannan from *Cryptococcus*, Fentanyl, Methadone, Buprenorphine, Lipopolysaccharides (LPS), Carbamazepine, Oxcarbazepine.

In a particular embodiment, the TLR4 agonist according to the invention is selected from the group consisting of the LPS or monophosphoryl lipid A (MPL).

Various TLR4 agonists are known in the art, including Monophosphoryl lipid A (MPLA), in the field also abbreviated to MPL, referring to naturally occurring components of bacterial lipopolysaccharide (LPS); refined detoxified endotoxin. For example, MPL is a derivative of lipid A from *Salmonella minnesota* R595 lipopolysaccharide (LPS or endotoxin). While LPS is a complex heterogeneous molecule, its lipid A portion is relatively similar across a wide variety of pathogenic strains of bacteria. MPL, used extensively as a vaccine adjuvant, has been shown to activate TLR4 (Martin M. et al., 2003. Infect Immun. 71(5):2498-507; Ogawa T. et al., 2002. Int Immunol. 14(11):1325-32). TLR4 agonists also include natural and synthetic derivatives of MPLA, such as 3-de-O-acylated monophosphoryl lipid A (3D-MPL), and MPLA adjuvants available from Corixa Corporation (Seattle, Wash.; see U.S. Pat. Nos. 4,436,727; 4,436,728; 4,987,237; 4,877,611; 4,866,034 and 4,912,094 for structures and methods of isolation and synthesis). A structure of MPLA is disclosed in U.S. Pat. No. 4,987,237. Non-toxic diphosphoryl lipid A (DPLA) may also be used, for example OM-174, a lipid A analogue of bacterial origin containing a triacyl motif linked to a diglucosamine diphosphate backbone. Another class of useful compounds are synthetic lipid A analogue pseudo-dipeptides derived from amino acids linked to three fatty acid chains (see for example EP 1242365), such as OM-197-MP-AC, a water soluble synthetic acylated pseudo-dipeptide (C55H107N4O12P). Non-toxic TLR4 agonists include also those disclosed in EP1091928, PCT/FR05/00575 or PCT/IB2006/050748. PCT/US2006/002906/WO 2006/083706; PCT/US 2006/003285/WO 2006/083792; PCT/US 2006/041865; PCT/US 2006/042051. TLR4 agonists also include synthetic compounds which signal through TLR4 other than those based on the lipid A core structure, for example an aminoalkyl glucosaminide 4-phosphate (see Evans J T et al. Expert Rev Vaccines. 2003 April; 2(2):219-29; or Persing et al. Trends Microbiol. 2002; 10(10 Suppl):532-7. Review). Other examples include those described in Orr M T, Duthie M S, Windish H P, Lucas E A, Guderian J A, Hudson T E, Shaverdian N, O'Donnell J, Desbien A L, Reed S G, Coler R N. MyD88 and TRIF synergistic interaction is required for TH1-cell polarization with a synthetic TLR4 agonist adjuvant. Eur J Immunol. 2013 May 29. doi: 10.1002/eji.201243124; Lambert S L, Yang C F, Liu Z, Sweetwood R, Zhao J, Cheng L, Jin H, Woo J. Molecular and cellular response profiles induced by the TLR4 agonist-based adjuvant Glucopyranosyl Lipid A. PLoS One. 2012; 7(12): e51618. doi: 10.1371/journal.pone.0051618. Epub 2012 Dec. 28.

As used herein, the term "TLR9 agonist" denotes a compound or a molecule that binds the Toll-like receptor 9 and actives it. According to the invention, a TLR9 agonist may be selected from the group consisting of CpG oligonucleotides (ODN) and its derivatives.

In particular embodiment, the TLR9 agonist is the CpG (ODN).

Examples of TLR9 agonists (include nucleic acids comprising the sequence 5'-CG-3' (a "CpG nucleic acid") in certain aspects C is unmethylated. The terms "polynucleotide," and "nucleic acid," as used interchangeably herein in the context of TLR9 agonist molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR9 agonist may be, for example, single-stranded DNA (ssDNA), double-stranded DNA (dsDNA), single-stranded RNA (ssRNA) or double-stranded RNA (dsRNA). TLR9 agonists also encompass crude, detoxified bacterial (e.g., mycobacterial) RNA or DNA, as well as enriched plasmids enriched for a TLR9 agonist. In some embodiments, a "TLR9 agonist-enriched plasmid" refers to a linear or circular plasmid that comprises or is engineered to comprise a greater number of CpG motifs than normally found in mammalian DNA. Examples of non-limiting TLR9 agonist-enriched plasmids are described in Roman et al. (1997). In general, a TLR9 agonist used in a subject composition comprises at least one unmethylated CpG motif. In some embodiments, a TLR9 agonist comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences. In other embodiments, a TLR9 agonist comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR9 agonist comprises (TCG)n, where n=1 to 3, at the 5' end of the nucleic acid. In other embodiments, the TLR9 agonist comprises (TCG)n, where n=1 to 3, and where the (TCG)n sequence is flanked by one nucleotide, two nucleotides, three nucleotides, four nucleotides, or five nucleotides, on the 5' end of the (TCG)n sequence. A TLR9 agonist of the present invention includes, but is not limited to, any of those described in U.S. Pat. Nos. 6,194,388; 6,207,646; 6,239,116; 6,339,068; and 6,406,705, 6,426,334 and 6,476,000, and published US Patent Applications US 2002/0086295, US 2003/0212028, and US 2004/0248837.

Examples of others TLR4 or TLR9 agonists are described in WO 2012/021834, the contents of which are incorporated herein by reference.

A variety of substances, used as supplemental antigens, can be added to the vaccine composition. For example, attenuated and inactivated viral and bacterial pathogens, purified macromolecules, toxoids, recombinant antigens, organisms containing a foreign gene from a pathogen, synthetic peptides, polynucleic acids, antibodies and tumor cells can be used to prepare (i) an immunogenic composition useful to induce an immune response in a individual or (ii) a vaccine useful for treating a pathological condition.

According to the invention the supplemental antigen gene may contain a signal sequence which allows the expression of the antigen in the membrane of the OMVs.

Therefore, the vaccine composition of the invention can be combined with a wide variety of antigens to produce a vaccine composition useful for inducing an immune response in an individual or in an animal.

Those skilled in the art will be able to select an antigen appropriate for treating a particular pathological condition and will know how to determine whether an isolated antigen is favored in a particular vaccine formulation.

In another particular embodiment, the vaccine composition according to the invention, further comprises one or more components selected from the group consisting of surfactants, absorption promoters, water absorbing polymers, substances which inhibit enzymatic degradation, alcohols, organic solvents, oils, pH controlling agents, preservatives, osmotic pressure controlling agents, propellants, water and mixture thereof.

The vaccine composition according to the invention can further comprise a pharmaceutically acceptable carrier. The amount of the carrier will depend upon the amounts selected for the other ingredients, the desired concentration of the antigen, the selection of the administration route, oral or parenteral, etc. The carrier can be added to the vaccine at any convenient time. In the case of a lyophilised vaccine, the carrier can, for example, be added immediately prior to administration. Alternatively, the final product can be manufactured with the carrier.

Examples of appropriate carriers include, but are not limited to, sterile water, saline, buffers, phosphate-buffered saline, buffered sodium chloride, vegetable oils, Minimum Essential Medium (MEM), MEM with HEPES buffer, etc.

Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines compositions.

Conventional preservatives can be added to the vaccine composition in effective amounts ranging from about 0.0001% to about 0.1% by weight. Depending on the preservative employed in the formulation, amounts below or above this range may be useful. Typical preservatives include, for example, potassium sorbate, sodium metabisulfite, phenol, methyl paraben, propyl paraben, thimerosal, etc.

The vaccine composition of the invention can be formulated as a solution or suspension together with a pharmaceutically acceptable medium.

Such a pharmaceutically acceptable medium can be, for example, water, phosphate buffered saline, normal saline or other physiologically buffered saline, or other solvent or vehicle such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside, such as Quil A.

Liquid dosage forms for oral administration of the vaccine composition of the invention include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the vaccine compositions of the invention for rectal or vaginal administration may be presented as a suppository, which may be prepared by mixing the active ingredient(s) with one or more suitable non-irritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Vaccine compositions of this invention suitable for parenteral administration comprise the active ingredient(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and non-aqueous carriers that may be employed in the vaccine compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents that delay absorption such as aluminum monostearate and gelatin.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly (orthoesters) and poly(anhydrides). Injectable formulations are also prepared by entrapping the active ingredient(s) in liposomes or microemulsions that are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The amount of OMVs, eventually supplemental antigen and adjuvant composition in the vaccine composition according to the invention are determined by techniques well known to those skilled in the pharmaceutical art, taking into consideration such factors as the particular antigen, the age, sex, weight, species, and condition of the particular animal or patient, and the route of administration.

While the dosage of the vaccine composition depends notably upon the antigen, species of the host vaccinated or to be vaccinated, etc., the dosage of a pharmacologically effective amount of the vaccine composition will usually range from about 0.01 µg to about 500 µg (and in particular 50 µg to about 500 µg) of the adjuvant compound of the invention per dose.

Although the amount of the particular antigenic substance in the combination will influence the amount of the adjuvant compound according to the invention, necessary to improve the immune response, it is contemplated that the practitioner can easily adjust the effective dosage amount of the adjuvant compound through routine tests to meet the particular circumstances.

The vaccine composition according to the invention can be tested in a variety of preclinical toxicological and safety studies well known in the art.

For example, such a vaccine composition can be evaluated in an animal model in which the antigen has been found to be immunogenic and that can be reproducibly immunized by the same route proposed for human clinical testing.

For example, the vaccine composition according to the invention can be tested, for example, by an approach set forth by the Center for Biologics Evaluation and Research/Food and Drug Administration and National Institute of Allergy and Infectious Diseases.

Those skilled in the art will know how to determine for a particular vaccine composition, the appropriate antigen payload, route of immunization, volume of dose, purity of antigen, and vaccination regimen useful to treat a particular pathological condition in a particular animal species.

In a vaccination protocol, the vaccine may be advantageously administered as a unique dose or preferably, several times e.g., twice, three or four times at week or month intervals, according to a prime/boost mode. The appropriate dosage depends upon various parameters.

As a general rule, the vaccine composition of the present invention is conveniently administered orally, parenterally (subcutaneously, intramuscularly, intravenously, intradermally or intraperitoneally), intrabuccally, intranasally, or transdermally, intralymphatically, intratumorally, intravesically, intraperitoneally and intracerebrally. The route of administration contemplated by the present invention will depend upon the antigen.

According to the invention, the vaccinal composition of the present invention may be used in human health or animal health. In other word, the vaccinal composition may be useful to prevent disease in human and animal.

Screening Method

Another object of the invention relates to a method for the screening of substances that may be useful for the prevention and treatment of infections by Enterobacteriaceae family comprising a step of determining the ability of a candidate substance to inhibit the expression of the gene hlyF of Enterobacteriaceae or the activity of the protein encoded by said genes.

Another object of the invention relates to a method for the screening of substances that may be useful for the prevention and treatment of infections by *Pseudomonas* family comprising a step of determining the ability of a candidate substance to inhibit the expression of the gene hlyF of *Pseudomonas* or the activity of the protein encoded by said genes In one embodiment, the candidate substance will be able to inhibit the epimerase activity of the hemolysin F.

Thus, the invention also relates to a method for the screening of substances that may be useful for the prevention and treatment of infections by Enterobacteriaceae family or *Pseudomonas* family comprising a step of determining the ability of a candidate substance to inhibit the epimerase activity of the hemolysin F protein of Enterobacteriaceae.

In one embodiment, the Enterobacteriaceae is an *Escherichia coli* or an ExPEC, APEC or NMEC.

In one embodiment, the method for the screening of substances that may be useful for the prevention and treatment of infections by Enterobacteriaceae family or *Pseudomonas* family which comprises the steps consisting of:

a) providing a composition comprising a Enterobacteriaceae or a *Pseudomonas* e.g. *Escherichia coli;* b) adding the candidate substance to be tested to the composition provided at step a), whereby providing a test composition;

c) comparing the activity of hlyF gene or the activity of proteins encoded by said gene in said test composition with the activity of the same hlyF gene or protein in the absence of said candidate substance; and d) selecting positively the candidate substance that inhibits the expression of hlyF gene or the activity of the protein encoded by said gene.

The method according to the invention wherein the inhibitor substance is selected for its in vivo activity.

In one embodiment, the inhibition of the gene expression according to the invention may be monitored by the production of the protein encoded by this gene.

The invention also encompasses methods for the screening of candidate substances that are based on the ability of said candidate substances to inhibit the activity of the protein encoded by the gene hlyF.

In other word, the invention consists to a method for the screening of substances that may be useful for the prevention and treatment of infections by Enterobacteriaceae family or *Pseudomonas* family which comprises the steps consisting of:

a) providing a composition comprising the proteins encoded by the gene hlyF;

b) adding the candidate substance to be tested to the composition provided at step a), whereby providing a test composition;

c) comparing the activity of said protein in said test composition with the activity of the protein in the absence of said candidate substance; and d) selecting positively the candidate substance that inhibits the activity of said protein.

Candidate substances that have been positively selected with the method below at the end of any one of the in vitro screening methods of the invention may then tested in various in vitro assays. Said in vitro assays may consist in testing the ability of the positively selected candidate substance to impact the uptake of iron by the Enterobacteriaceae in an in vitro test.

In another embodiment, the candidate substances may be tested. The hemolytic ClyA toxin is known to be delivered to host cells via OMVs. Strain MG1655 produces a functional ClyA toxin. The production of OMVs will be monitored by dropping purified OMVs from each strain grown in the presence of potential inhibitors, on to the sheep blood agar plate, followed by incubation for 24 h at 37° C. The presence of hemolysis will reflect the production of OMVs, whereas the absence of hemolysis will reflect the absence of production of OMVs. Thus, activity of the candidate substance will be tested by monitoring the production or not of OMVs.

In another embodiment, a candidate substance to be tested inhibits the hemolytic function activity of the protein encoded by the gene hlyF, when the candidate substance is present, is lower than when said enzyme is used without the candidate substance under testing.

This invention also encompasses methods for the screening of candidate substances, that are based on the ability of said candidate substances to bind to a protein encoded by the gene hlyF as defined herein, thus methods for the screening of potentially substances that may be useful for the prevention and treatment of infections by Enterobacteriaceae family or *Pseudomonas* family.

The binding assays can be performed in a variety of formats, including protein-protein binding assays, biochemical screening assays, immunoassays, and cell-based assays, which are well characterized in the art.

All binding assays for the screening of candidate substances that may be useful for the prevention and treatment of infections by Enterobacteriaceae family or *Pseudomonas* family are common in that they comprise a step of contacting the candidate substance with a protein as defined herein, under conditions and for a time sufficient to allow these two components to interact.

These screening methods also comprise a step of detecting the formation of complexes between said protein encoded by the gene hlyF and said candidate substances.

Thus, screening for substances that may be useful for the prevention and treatment of infections by Enterobacteriaceae family or *Pseudomonas* family includes the use of two partners, through measuring the binding between two partners, respectively a protein as defined herein and the candidate substance.

In binding assays, the interaction is binding and the complex formed between a protein encoded by the gene hlyF as defined above and the candidate substance that is tested can be isolated or detected in the reaction mixture. In a particular embodiment, the protein as defined above or alternatively the anti-Enterobacteriaceae family or the or anti-*Pseudomonas* family candidate substance is immobilized on a solid phase, e.g., on a microtiter plate, by covalent or non-covalent attachments. Non-covalent attachment generally is accomplished by coating the solid surface with a solution of the protein of the invention and drying. Alternatively, an immobilized antibody, e.g., a monoclonal antibody, specific for the protein of the invention to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The binding of the anti-Enterobacteriaceae family candidate or the anti-*Pseudomonas* family candidate to a protein of the invention may be performed through various assays, including traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, 1989; Chien et al., 1991) as disclosed by Chevray and Nathans, 1991. Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for .beta.-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Thus, another object of the invention consists of a method for the screening of substances that may be useful for the prevention and treatment of infections by Enterobacteriaceae family or *Pseudomonas* family, wherein said method comprises the steps of:
  (i) providing a candidate substance;
  (ii) assaying said candidate substance for its ability to bind to the protein of the invention.

The same method may also be defined as a method for the screening of substances that may be useful for the prevention and treatment of infections by Enterobacteriaceae family or *Pseudomonas* family, wherein said method comprises the steps of:
  (i) contacting a candidate substance with a protein of the invention;
  (ii) detecting the complexes eventually formed between said protein and said candidate substance.

Thus, any substance that has been shown to behave like an inhibitor of the genes or proteins according to the invention, after positive selection at the end of any one of the screening methods that are disclosed previously in the present specification, may be further assayed for his in vivo activity.

Consequently, any one of the screening methods that are described above may comprise a further step of assaying the positively selected inhibitor substance for its in vivo activity. However, other non human mammals may be used.

Non human mammals encompass rodents like mice, rats, rabbits, hamsters, guinea pigs. Non human mammals and also cats, dogs, pigs, veals, cows, sheep, goats. Non human mammals also encompass primates like macaques and baboons.

Thus, another object of the present invention consists of a method for the in vivo screening of a candidate substance that may be useful for the prevention and treatment of infections by Enterobacteriaceae family or *Pseudomonas* family which comprises the steps of:
  a) performing a method for the in vitro screening of a substance as disclosed in the present specification, with a candidate substance; and
  b) assaying a candidate substance that has been positively selected at the end of step a) for its in vivo activity.

In other words, the invention consists to a method for the screening of substances that may be useful for the prevention and treatment of infections by Enterobacteriaceae family or *Pseudomonas* family which comprises the steps consisting of:
  a) using an animal model with a disease induced by Enterobacteriaceae or *Pseudomonas*;
  b) adding the candidate substance to be tested to the animal model;
  c) comparing the effect of the candidate substance on the animal model with another animal model which has not received any candidate substance or which has received a placebo; and
  d) selecting positively the candidate substance that improve the survival of the animal model.

Candidate substances that have been positively selected at the end of any one of the in vitro screening methods of the invention may then tested in various in vivo assays. Said in vivo assays may consist in testing the ability of the positively selected candidate substance to impact the virulence of Enterobacteriaceae or *Pseudomonas* in a mouse model. Thus, any substance that has been shown to behave like an inhibitor of a protein, after positive selection at the end of any one of the in vitro screening methods that are disclosed previously in the present specification, may be further in vivo assayed.

Before in vivo administration to a mammal, the inhibitor substances selected through any one of the in vitro screening methods above may be formulated under the form of pre-pharmaceutical compositions. The pre-pharmaceutical compositions can include, depending on the formulation desired, pharmaceutically acceptable, usually sterile, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution.

In addition, the test composition or formulation may also include other carriers, adjuvants, or nontoxic, nontherapeutic, nonimmunogenic stabilizers and the like.

Compositions comprising such carriers can be formulated by well known conventional methods. These test compositions can be administered to the mammal at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by taking into account, notably, clinical factors. As is well known in the medical arts, dosages for any one mammal depends upon many factors, including the mammal's size, body surface area, age, the particular substance to be administered, sex, time and route of administration and general health. Administration of the suitable pre-pharmaceutical compositions may be effected by different ways, e.g., by intravenous, intraperitoneal, subcutaneous, intramuscular, topical or intradermal administration. If the regimen is a continuous infusion, it should also be in the range of 1 ng to 10 mg units per kilogram of body weight per minute, respectively. Progress can be monitored by periodic assessment. The pre-pharmaceutical compositions of the invention may be administered locally or systemically. Administration will generally be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, anti-oxidants, chelating agents, and inert gases and the like.

The inhibitor substances may be employed in powder or crystalline form, in liquid solution, or in suspension.

The injectable pre-pharmaceutical compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline, or another injectable liquid, e.g., peanut oil for intramuscular injections. Also, various buffering agents, preservatives and the like can be included.

Topical applications may be formulated in carriers such as hydrophobic or hydrophilic base formulations to provide ointments, creams, lotions, in aqueous, oleaginous, or alcoholic liquids to form paints or in dry diluents to form powders.

Oral pre-pharmaceutical compositions may take such forms as tablets, capsules, oral suspensions and oral solutions. The oral compositions may utilize carriers such as conventional formulating agents and may include sustained release properties as well as rapid delivery forms.

Generally, all animals are sacrificed at the end of the in vivo assay. For determining the in vivo activity of the inhibitor substance that is tested, blood or tissue samples of the tested animals such as brain samples are collected at determined time periods and bacteria counts are performed, using standard techniques, such as staining fixed slices of the collected tissue samples or plating the collected blood samples and counting the bacterial colonies formed. Then, the values of the bacteria counts found for animals having been administered with increasing amounts of the inhibitor substance tested are compared with the value(s) of bacteria count(s) obtained from animals that have been injected with the same number of bacteria cells but which have not been administered with said inhibitor substance.

The invention will be further illustrated by the following figures and examples. However, these examples and figures should not be interpreted in any way as limiting the scope of the present invention.

FIGURES

FIG. 1. Competition between APEC $\chi$7122 strain and hlyF derivatives for colonization of chicken.

Chickens were co-infected in the left air-sacs with equal amounts of $\chi$7122$\Delta$lacZYA strain and either $\chi$7122$\Delta$hlyF or $\chi$7122$\Delta$hlyF complemented strain. Blood samples were collected from each chicken 6 h, 24 h and 48 h post-inoculation. Animals were euthanized 48 h post-inoculation and necropsied. The proportion of each strain in blood and tissues was monitored and results are represented as the log 10 competitive indexes (CI). The CI represents the relative numbers of the two tested strains from the tissues sampled compared to the initial numbers of the strains in the inoculum. Negative CI values indicate a decreased capacity for the mutant or complemented strain to compete with the reference strain ($\chi$7122$\Delta$lacZYA). Horizontal bars indicate the mean log 10 CI values. Each data point represent a sample from an individual chicken. Statistically significant decreases in CI were determined by the Wilcoxon matched-pair test. The Mann-Whitney test was used to determine statistical differences between CI values of the $\chi$7122$\Delta$hlyF strain and CI values of the $\chi$7122$\Delta$hlyF complemented strain (*, $P<0.05$; , $P<0.005$; *, $P<0.0001$).

Figure 2:
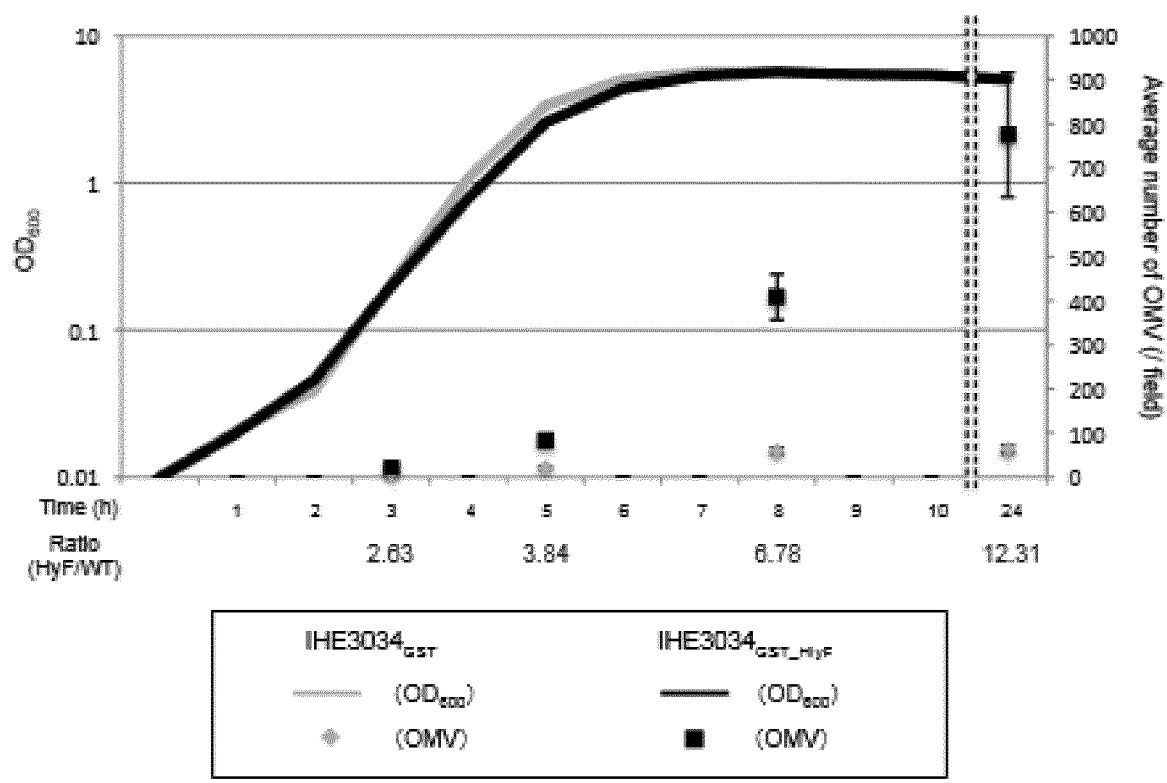

FIG. 2. Role of the physiological state of E. coli for the production of OMVs.

A quantification of the relative production of OMVs was determined in relation with the growth phase of the bacterial culture.

Figure 3:
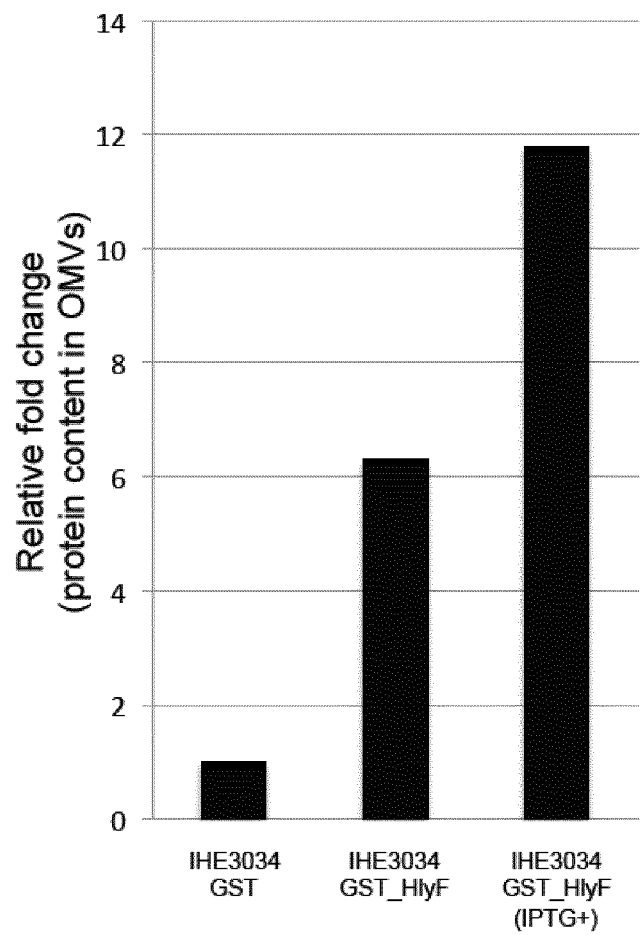

FIG. 3. Protein profile of OMVs extracted from E. coli strain IHE3034 expressing or not HlyF.

OMVs were harvested from strains grown for 24 h. The proteins contained in OMVs were separated by SDS-PAGE with 12% resolving gel. The gel was stained with SYPRO Ruby Protein Gel stain and the bands were quantified by using Gel Doc XR+.

Figure 4:
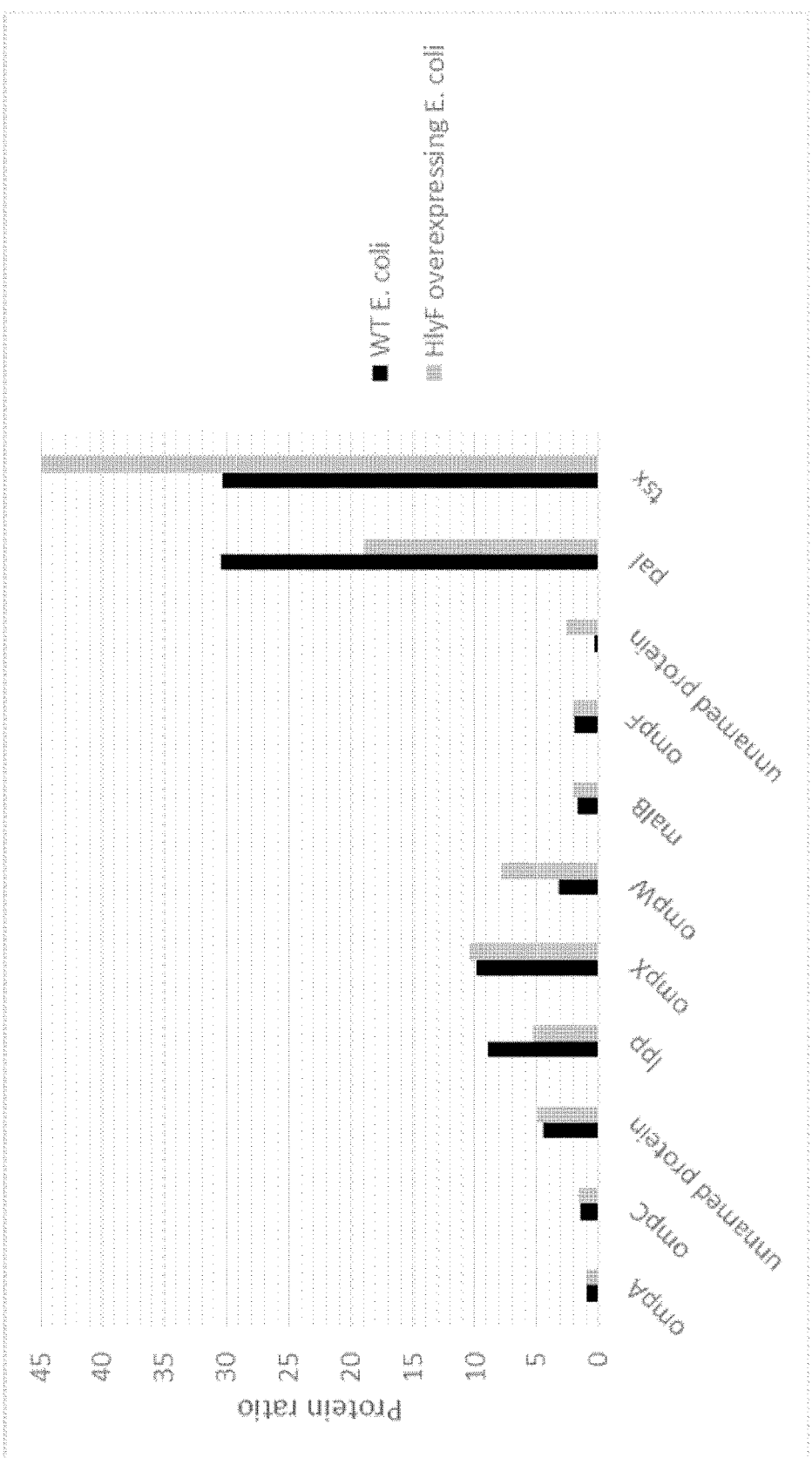

FIG. 4: Comparative proteomic analysis of OMVs produced by wild type E. coli and the same strain overproducing HlyF.

The 11 most highly represented proteins in wt OMVs are shown. Protein quantifications were normalized based on the amount of the outer membrane protein OmpA present in OMVs.

EXAMPLE

Material & Methods
Bacterial Strains

For routine bacterial cultivation, *Escherichia coli* were grown aerobically at 37° C. in Luria-Bertani (LB) broth, supplemented with ampicillin (100 µg mL-1) when necessary.

Chemicals Antibiotics and reagents were used at the following concentrations: nalidixic acid, 40 µg mL-1; gentamicin, 15 µg mL-1 ampicillin 100 µg mL-1; kanamycin 30 µg mL-1; trimethoprin, 10 µg mL-1; diaminopimelic acid (DAP), 50 µg mL-1.

Construction of Mutant and Complemented Strains

ΔhlyF mutants were generated by the method described by Datsenko and Wanner [Datsenko et al., 2000]. Briefly, using a Red recombination procedure, hlyF was deleted and replaced by a kanamycin resistance cassette. Plasmid pKD4 was used to amplify the hlyF::kan allele using primers CMD1043 and CMD1044. The replacement of hlyF by the kanamycin resistance cassette was confirmed by PCR using primers CMD710 and CMD928.

The mutant strain was complemented by inserting the hlyF gene at the attTn7 site of the chromosome as described by Crépin et al. [Crepin S et al., 2012]. Briefly, hlyF gene and its native promoter were amplified from χ7122 strain using primers CMD1630/CMD1631. The amplified product was then inserted into the pUCM-T vector (Bio Basic) and recombinant plasmid was introduced into E. coli DH5a by electroporation. Constructions were verified by PCR using primers CMD1630/CMD1631 and by restriction profile. This plasmid was then digested with XhoI. The fragment was inserted into the multiple cloning site (MCS) of the mini-Tn7-containing vector pGP-Tn7-Gm digested with the corresponding restriction enzyme, generating plasmid pIJ452 (hlyF gene in the same direction as aacC1 gene). This construction was verified by PCR using primers CMD1630, CMD1631 and CMD1420, and by restriction profile. Strain MGN-617 containing pIJ452 was then conjugated overnight at 30° C. on LB agar plates supplemented with DAP with the ΔhlyF mutant containing the plasmid pIJ360 encoding the transposases tnsABCD required for transposition of Tn7 at the attTn7 site. The bacterial lawn was then serially diluted, spread on LB agar plates supplemented with gentamicin and incubated at 37° C. Colonies were verified for sensitivity to trimethoprim and ampicillin, indicating the likelihood of integration at attTn7 and loss of pIJ360. Insertion into the attTn7 site was then verified by PCR using primers CMD1630, CMD1631, CMD1420 and CMD156.

Construction of hlyF-Cloning Vector

The entire hlyF gene from plasmid of E. coli strain SP15 was amplified by PCR with the hlyF_EcoRI_GST and hlyF_XhoI_GST primers. The amplicon was digested with EcoRI and XhoI and ligated to the EcoRI/XhoI double digested pGEX-6P-1 (pGST; GE Healthcare), a pBR322-derived vector carrying the tac promoter, ampicillin resistance gene and GST gene encoding glutathione S-transferase to generate pGEX-6P-1::hlyF (pGST-HlyF). The nucleotide sequence of the hlyF gene cloned into pGEX-6P-1 was checked. The pGST or pGST-HlyF was introduced into E. coli strains MG1655, BL21 and IHE3034 by electroporation, and the GST protein- or GST-HlyF fusion protein-expressing strains (MG1655GST, BL21GST, IHE3034GST, MG1655GST_HlyF, BL21GST_HlyF, and IHE3034GST_HlyF) were used in this study.

Site-Directed Mutagenesis Targeted for Catalytic Activity Site of Epimerase

The substitutions Y163F and K167A were introduced into HlyF cloned into pGEX6P-1 plasmid using Quick-ChangeII Site-Directed Mutagenesis kit (Stratagene, La Jolla, Calif.) and primers hlyF-sdm-R and hlyF-sdm-F. The resulting plasmid pGST-HlyF-sdm was introduced into E. coli strain IHE3034 by transformation.

Purification of OMVs

The bacterial cells were grown aerobically at 37° C. in LB medium supplemented with ampicillin (100 µg mL-1). When required, IPTG 0.05 mM was added to the culture. The cells were harvested (3 h, 5 h, 8 h, and 24 h) and centrifuged at 7,000 r.p.m. for 10 min at 4° C. Then the supernatant was filtrated with 0.45 µm pore-size filter to obtain cell-free supernatant. The filtrated supernatant was centrifuged at 150,000×g for 3 h at 4° C., and the pellet was suspended in 20 mM Tris-HCl (pH 8.0).

OMV Protein Profile

The proteins contained in OMV were separated by SDS-PAGE with 12% resolving gel. The gel was stained with SYPRO Ruby Protein Gel stain (Sigma) according to the manufacturer's instructions. The bands were visualized by using Gel Doc XR+ (Bio-Rad) and analyzed by Image Lab 4.1 for relative quantification of protein content in OMVs with consideration of OD600 nm.

Transmission Electron Microscopy (TEM) and Semi-Quantitative Analysis of the Amount of OMVs Produced TEM was used for the observation of OMVs released from E. coli. Briefly, 5 µL of OMV solution was dropped onto collodion-coated copper grid and blotted using filter paper after 5 min. The grid was then stained for 30 s by inverting onto a drop of 2% uranyl acetate solution and blotted using filter paper. The OMVs were visualized by transmission electron microscopy HT7700 (HITACHI) operating 80 kV. For the semi-quantitative analysis of OMVs, the number of OMVs present in 10 fields was counted using ImageJ software (70,000-fold magnification). The average number of OMVs per field was determined. This analysis was repeated at least twice.

Cytotoxic Assay in HeLa Cell

HeLa cells were maintained by serial passage in DMEM supplemented with 10% fetal calf serum (FCS), non-essential amino acids and 50 µg/mL gentamicin. HeLa cells were dispensed in 96-well cell culture plate (5×103 cells/wells). Serial dilutions of OMVs solution were added to HeLa cells and incubated for 24 h at 37° C. at 5% CO2.

Western-Blotting Analysis

Proteins were separated on 4-12% NuPage gradient gel (Invitrogen), transferred to nitrocellulose membranes, blocked with 10% milk buffer and probed with anti-CdtABC (home-made rabbit polyclonal antibody), followed by horseradish peroxidase-conjugated secondary antibodies and chemiluminescent autoradiography.

Hemolytic Activity Assay

The hemolytic ClyA toxin is known to be delivered to host cells via OMVs [16]. Strain MG1655 produces a functional ClyA toxin. Strain BL21 produces a non-functional ClyA toxin. 5 µl of purified OMVs from each strain were dropped on to the sheep blood agar plate, and then incubated for 24 h at 37° C.

Experimental Infections of Chickens

The housing, husbandry and slaughtering conditions complied with the Canadian Council on Animal Care (CCAC) and the Association for Assessment and Accreditation of Laboratory Animal Care International (AAALAC) guidelines for the care and use of laboratory animals. The experimental protocol for experimental colibacillosis was approved by Institutional Committee for Protection of Animals [Comité Institutionnel de Protection des Animaux (CIPA) Centre National de Biologie Expérimentale] under number CIPA 1103-10.

For co-infection experiments, 3-week-old White Leghorn specific-pathogen-free chickens (Canadian Food Inspection Agency, Ottawa, Canada) were inoculated in the left thoracic air sac with a 0.1 ml suspension containing a mixture of equal numbers of QT51 (virulent ΔlacZYA derivative of χ7122) and either QT1880 (χ7122ΔhlyF) or QT3363 (χ7122ΔhlyF complemented) (each approximately at 5×106 CFU) in brain heart infusion medium. The inoculum was prepared from an overnight culture of each strain grown in 10 ml brain heart infusion medium at 37° C. with slight agitation. Experimental infections were carried out as previously described [14]. Blood samples were collected aseptically from each chicken 6 h, 24 h and 48 h post-inoculation and serial dilutions were plated onto MacConkey-lactose (Difco) agar plates for bacterial quantification. Animals were euthanized 48 h post-inoculation and necropsied. Samples of the right lung, liver and spleen were collected and weighted. After homogenization in sterile saline with gelatin (BSG; per liter, 8.5 g NaCl, 0.3 g KH2PO4, 0.6 g Na2HPO4, 0.1 g gelatin), serial dilutions were plated onto MacConkey-lactose agar plates for bacterial quantification. Competitive indexes (CI) were calculated following Freter et al.'s method using QT51 as the reference strain.

Phylogenetic Tree Construction

Amino acid sequences of HlyF from each plasmid were aligned by using COBALT (Constraint-based Multiple Protein Alignment Tool). Molecular phylogenetic trees were constructed using both neighbor-joining method using MEGA 5.05. Poisson model and 1000 bootstrap replications were applied for the analysis.

Statistical Analyses

All data were analyzed with the Prism 5.01 software package (GraphPad Software, San Diego, Calif., USA). A Mann-Whitney test and a Wilcoxon match-paired test were used to determine statistical significance.

Results

HlyF is Highly Conserved on Virulent Plasmids

To determine the prevalence of HlyF in bacteria, blast search was performed and revealed that genes homologous to hlyF are distributed in Enterobacteriaceae (*Cronobacter, Serratia, Enterobacter, Klebsiella*, and *Pseudomonas*) (data not shown). Noteworthy, the hlyF gene is present on large virulence plasmids harbored by pathogenic *E. coli* and *Salmonella enterica* (data not shown). The maximum-likelihood tree constructed using the nucleotide sequences of hlyF showed that the sequence of hlyF is highly conserved in these plasmids (data not shown).

To gain more information about genetic similarities of the hlyF genes and their flanking regions, the hlyF gene with adjacent region was compared in 14 different plasmids in a variety of *E. coli* and *S. enterica* strains (data not shown). This revealed that the cluster of genes flanking hlyF is highly conserved in all plasmids (data not shown).

HlyF Contributes to Virulence of APEC During Infection of Chickens

The precise role of HlyF in virulence being unknown, we investigated the importance of hlyF gene for the virulence of the avian pathogenic *Escherichia coli* (APEC) strain χ7122 in chickens. Coinfection experiments were performed between the wild-type χ7122ΔlacZYA strain and the ΔhlyF mutant (FIG. 1). The χ7122ΔlacZYA strain is as virulent as the χ7122 wild-type parent and presented no statistical difference in chicken colonization. The ΔhlyF mutant was attenuated and showed a significantly reduced competitive index (CI) with the wild-type strain in the blood and liver of chickens (FIG. 1). This mutant was outcompeted in the blood 6.8-fold, 4.6-fold and 3.5-fold at 6 h post-infection (p.i.), 24 h p.i. and 48 h p.i., respectively (closed circles). In addition, whereas the ΔhlyF mutant was not attenuated in lungs and spleen, it was outcompeted 3.3-fold in the liver (FIG. 1). To confirm the role of HlyF in the virulence of APEC χ7122, coinfection experiments were performed between the wild-type χ7122ΔlacZYA strain and the ΔhlyF complemented strain. The complemented strain regained competitive colonization of blood and liver with the wild-type strain, as log 10 CI were not significantly different from 0 (FIG. 1, open circles). Moreover, CI obtained with the complemented strain were significantly different from CI obtained with the ΔhlyF mutant in the blood of infected chickens (P=0.0272 at 6 h p.i., P=0.033 at 24 h p.i., P=0.0033 at 48 h p.i., FIG. 1). This demonstrated the ability of hlyF to improve competitive fitness in the blood. Altogether, these data evidenced that HlyF contributes to virulence of APEC during infection of chickens.

HlyF is Involved in the Production of Outer Membrane Vesicles

To investigate the involvement of HlyF in the production of OMVs, *E. coli* strain IHE3034 devoid of endogenous hlyF gene was transformed with plasmid pGST and plasmid pGST-HlyF, and *E. coli* strain SP15 was disrupted for the hlyF gene. OMVs were isolated from the resulting *E. coli* strains IHE3034GST, IHE3034GST_HlyF, SP15 and SP15ΔhlyF and were observed by transmission electron microscopy (TEM) (data not shown). This revealed that the amount of OMVs was higher in strain IHE3034GST_H1yF compared to strain IHE3034GST and higher in wild type SP15 strain compared to its ΔhlyF mutant (data not shown). A time-course analysis of the production of OMVs was performed in strains IHE3034GST and IHE3034GST_HlyF (FIG. 2). This showed that the amount of OMVs produced by both strains was gradually increased with cultivation time (data not shown). Nevertheless, in strain IHE3034GST HlyF, the amount of OMVs produced was 12 times higher than that of strain IHE3034GST at 24h cultivation (data not shown).

The proteins located in the OMVs were extracted, run on a SDS-PAGE gel (data not shown) and quantified (FIG. 3). This revealed that the amount of total proteins significantly increased in *E. coli* strain IHE3034 when hlyF was overexpressed (6.3-fold, FIG. 3). Moreover, the increase of total proteins was amplified upon induction of the expression of the hlyF gene with IPTG (11.7-fold, FIG. 3).

Altogether, these data evidenced that HlyF is involved in the production of OMVs, and that the production of OMVs is significantly increased at stationary phase.

HlyF Encodes a Putative Epimerase

In order to predict a putative enzymatic function for HlyF, conserved domains were searched by using the Simple Modular Architecture Research Tool (SMART) (smart-.embl-heidelberg.de/). Two distinct motifs were identified, i.e. a NAD-binding site (1e-48) and an epimerase domain (1.3e-7). A well-known epimerase is GalE, a UDP-galactose 4-epimerase which catalyzes the conversion of UDP-galactose to UDP-glucose during galactose metabolism. A comparison of amino acid sequence between HlyF (from plasmid pAPEC-1) and GalE (from *E. coli* strain MG1655) revealed that the sequence identity (aa) of HlyF and GalE is low. Nevertheless, the NAD-binding sites (GXXGXXG) and the catalytic domain site (YXXXK) are conserved (data not shown). This suggested that HlyF could have a function similar to GalE that was reported to be involved in the modification of the bacterial outer membrane through the production of outer membrane vesicles (OMVs).

HlyF is not Secreted in the Outer Membrane Vesicles

To determine whether the HlyF protein was directly involved in the cytotoxic effect of OMVs, we studied the localization of HlyF upon overexpression (data not shown).

Total proteins were isolated from fractionated cultures of *E. coli* strains MG1655GST and MG1655GST_HlyF and were analyzed by western blotting using anti-GST antibodies. This showed that when the hlyF gene was expressed, the HlyF protein was detected in the cell lysate but not in the supernatant (data not shown). This indicated that HlyF is not directly involved in the cytotoxic activity of the expressing strain.

The Epimerase Domain of HlyF is Required for the Production of Outer Membrane Vesicles In order to investigate whether the putative epimerase function of HlyF was involved in the production of OMVs, the putative catalytic site of HlyF was mutated by site-directed mutagenesis on plasmid pGST-HlyF. The resulting plasmid was transformed into *E. coli* strain IHE3034. The production of OMVs was analyzed in strain IHE3034GST_HlyF_sdm (data not shown).

These data evidenced that the epimerase domain of HlyF is required for the HlyF-dependent production of OMVs.

The Increased HlyF-Dependent Production of Outer Membrane Vesicles is Associated with Increased Release of Toxins Because OMVs are platforms for bacterial virulence factors such as cytolethal distending toxin (CDT), cytotoxic necrotizing factor 1 (CNF1), labile toxin (LT), heat-stable toxin (ST), and cytolysin A (ClyA), we investigated whether HlyF-dependent increased production of OMVs could be associated with increased release of toxins.

Two laboratory *E. coli* K12 strains, i.e. strain MG1655 that harbors an endogenous functional clyA gene, and strain BL21 that harbors a mutated clyA gene, were transformed with pGST or pGST-HlyF. The resulting MG1655GST, MG1655GST_HlyF, BL21GST and BL21GST_HlyF strains were analyzed for their hemolytic activity on blood agar plate (data not shown). This revealed that any strain but strain MG1655GST_HlyF exhibited a hemolytic phenotype. The strong hemolytic phenotype displayed by strain MG1655GST_HlyF indicated that ClyA-derived hemolysis was enhanced by the increased production of HlyF-induced OMVs.

We also tested whether the production of CDT was related to the production of OMVs (data not shown). The presence of the CDT toxin was studied in OMVs and in culture supernatants devoid of OMVs in *E. coli* wild type strain IHE3034 and its cdtB mutant derivative altered for the production of CDT, expressing or not hlyF. When hlyF was overexpressed, the amount of CDT protein was higher in the OMV fraction but not in the culture supernatant (data not shown). Therefore, the release of CDT was also augmented upon hlyF overexpression.

Comparative Analysis of OMVs Produced by Wild Type *E. coli* and the Same Strain Overproducing HlyF (FIG. 4).

This comparison revealed that some proteins are present in the different OMVs in the same proportion. On the contrary, OMVs produced subsequently to HlyF overexpression contain less Lpp and Pal but more OmpW and Tsx protein as compared to wt OMVs. Thus, OMVs produced by wild type *E. coli* and OMVs produced by the same strain but overproducing HlyF show different proteomic profiles and thus are not the same.

The *Escherichia coli* outer membrane protein Tsx functions as the receptor for colicin K and a number of T-even-type bacteriophages (Schneider et al. 1993). Therefore the increasing amount of Tsx protein in induced OMVs will serve as a lure for colicin K and phages that could be directed towards OMVs and away from *E. coli* cells.

OmpW protein was reported to protect bacteria against host phagocytosis. In addition, expression of ompW is regulated by iron, which implies that the resistance provided by OmpW may be an important factor in iron-related infectious diseases. Furthermore, OmpW has been identified as a protective antigen that protects mice against bacterial infection and is therefore a promising target for vaccine development against infectious diseases (Wu et al., 2013). Altogether, these data suggest that induced OMVs will stimulate immune system in a manner different than the wild tune OMVs.

REFERENCES

Throughout this application, various references describe the state of the art to which this invention pertains. The disclosures of these references are hereby incorporated by reference into the present disclosure.

Ahmed A M, Shimamoto T (2013) Molecular characterization of multidrug-resistant avian pathogenic *Escherichia coli* isolated from septicemic broilers. Int J Med Microbiol 303: 475-483.

Berleman James and Manfred Auer. The role of bacterial outer membrane vesicles for intraand interspecies delivery. Environmental Microbiology (2013) 15(2), 347-354.

Crepin S, Harel J, Dozois C M (2012) Chromosomal complementation using Tn7 transposon vectors in Enterobacteriaceae. Appl Environ Microbiol 78: 6001-6008.

Datsenko K A, Wanner B L (2000) One-step inactivation of chromosomal genes in *Escherichia coli* K-12 using PCR products. Proc Natl Acad Sci USA 97: 6640-6645.

Dobrindt U, Hacker J (2008) Targeting virulence traits: potential strategies to combat extraintestinal pathogenic *E-coli* infections. Curr Opin Microbiol 11: 409-413.

Kaczmarek A, Budzynska A, Gospodarek E (2012) Prevalence of genes encoding virulence factors among *Escherichia coli* with K1 antigen and non-K1 *E. coli* strains. J Med Microbiol 61: 1360-1365.

Peigne C, Bidet P, Mahjoub-Messai F, Plainvert C, Barbe V, et al. (2009) The plasmid of *Escherichia coli* strain S88 (O45:K1:H7) that causes neonatal meningitis is closely related to avian pathogenic *E. coli* plasmids and is associated with high-level bacteremia in a neonatal rat meningitis model. Infect Immun 77: 2272-2284.

Skyberg J A, Johnson T J, Johnson J R, Clabots C, Logue C A, et al. (2006) Acquisition of avian pathogenic *Escherichia coli* plasmids by a commensal *E coli* isolate enhances its abilities to kill chicken embryos, grow in human urine, and colonize the murine kidney. Infect Immun 74: 6287-6292.

Schlosser-Silverman El, Elgrably-Weiss M, Rosenshine I, Kohen R, Altuvia S. Characterization of *Escherichia coli* DNA lesions generated within J774 macrophages. J Bacteriol. 2000 September; 182(18):5225-30.

Schneider H, Fsihi H, Kottwitz B, Mygind B, Bremer E. Identification of a segment of the *Escherichia coli* Tsx protein that functions as a bacteriophage receptor area. J Bacteriol. 1993 175(10):2809-17.

Wieser Andreas, Eva Romann, Giuseppe Magistro, Christiane Hoffmann, Dominik No¨renberg, Kirsten Weinert, and So¨ren Schubert. A Multiepitope Subunit Vaccine Conveys Protection against Extraintestinal Pathogenic *Escherichia coli* in Mice. INFECTION AND IMMUNITY, August 2010, p. 3432-3442.

Wu Xian-Bin et al. Outer membrane protein OmpW of *Escherichia coli* is required for resistance to phagocytosis. Research in Microbiology, 164(8): 848-855, 2013.

The invention claimed is:

1. An ex vivo method for producing outer membrane vesicles (OMVs) comprising
expressing or overexpressing a hemolysin F gene (hlyF) in gram-negative bacterium; and
recovering the OMVs from the gram-negative bacterium.

2. The ex vivo method according to the claim 1, wherein said expressing or overexpressing step comprises:
   a) transforming the gram-negative bacterium with the hlyF gene and/or overexpressing an endogenous hlyF gene of the gram-negative bacterium; and
   b) cultivating the gram-negative bacterium in an appropriate culture medium;
and wherein said recovering step comprises:
   c) centrifuging the culture medium to remove bacteria and obtain a supernatant comprising OMVs;
   d) filtering the supernatant; and
   e) centrifuging filtered supernatant to obtain a pellet of OMVs.

3. The ex vivo method according to claim 1 wherein the gram-negative bacterium is an Enterobacteriaceae.

4. The ex vivo method according to claim 3 wherein the Enterobacteriaceae is an *Escherichia coli*.

5. OMVs having a different proteomic profile than OMVs produced by wild type gram-negative bacteria, wherein the OMVs are obtained by
   a) transforming a gram-negative bacterium with a hlyF gene;
   b) cultivating the gram-negative bacterium in an appropriate culture medium;
   c) centrifuging the culture medium to remove bacteria and obtain a supernatant comprising OMVs;
   d) filtering the supernatant; and
   e) centrifuging filtered supernatant to obtain a pellet of OMVs, wherein the OMVs
   contain at least 50% more Tsx protein than OMVs produced by wild type gram-negative bacteria; and/or
   contain at least twice as much OmpW protein than OMVs produced by wild type gram-negative bacteria; and/or
   contain at least 50% less Lpp protein than OMVs produced by wild type gram-negative bacteria; and/or
   contain at least 30% less Pal protein than OMVs produced by wild type gram-negative bacteria.

6. A vaccine composition comprising an adjuvant and OMVs having a different proteomic profile than OMVs produced by wild type gram-negative bacteria, wherein the OMVs are obtained by
   a) transforming a gram-negative bacterium with a hlyF gene;
   b) cultivating the gram-negative bacterium in an appropriate culture medium;
   c) centrifuging the culture medium to remove bacteria and obtain a supernatant comprising OMVs;
   d) filtering the supernatant; and
   e) centrifuging filtered supernatant to obtain a pellet of OMVs, wherein the OMVs
   contain at least 50% more Tsx protein than OMVs produced by wild type gram-negative bacteria; and/or
   contain at least twice as much OmpW protein than OMVs produced by wild type gram-negative bacteria; and/or contain at least 50% less Lpp protein than OMVs produced by wild type gram-negative bacteria; and/or
contain at least 30% less Pal protein than OMVs produced by wild type gram-negative bacteria.

7. The vaccine composition according to claim 6 wherein the adjuvant is a TLR4 agonist or a TLR9 agonist.

* * * * *

SEQUENCE LISTING

<160> NUMBER OF SEQ ID NOS: 14

<210> SEQ ID NO 1
<211> LENGTH: 22
<212> TYPE: PRT
<213> ORGANISM: Escherichia coli

<400> SEQUENCE: 1

Met Lys Met Thr Arg Leu Tyr Pro Leu Ala Leu Gly Gly Leu Leu Leu
1               5                   10                  15

Pro Ala Ile Ala Asn Ala
            20

<210> SEQ ID NO 2
<211> LENGTH: 21
<212> TYPE: PRT
<213> ORGANISM: Escherichia coli

<400> SEQUENCE: 2

Met Lys Val Lys Val Leu Ser Leu Leu Val Pro Ala Leu Leu Val Ala
1               5                   10                  15

Gly Ala Ala Asn Ala
            20

<210> SEQ ID NO 3
<211> LENGTH: 22
<212> TYPE: PRT
<213> ORGANISM: Erwinia carotovora

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 4
<211> LENGTH: 21
<212> TYPE: PRT
<213> ORGANISM: Escherichia coli

<400> SEQUENCE: 4

Met Lys Lys Thr Ala Ile Ala Ile Ala Val Ala Leu Ala Gly Phe Ala
1               5                   10                  15

Thr Val Ala Gln Ala
            20

<210> SEQ ID NO 5
<211> LENGTH: 23
<212> TYPE: PRT
<213> ORGANISM: Escherichia coli

<400> SEQUENCE: 5

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 6
<211> LENGTH: 28
<212> TYPE: PRT
<213> ORGANISM: Bacillus sp.

```
<400> SEQUENCE: 6

Met Phe Lys Phe Lys Lys Phe Leu Val Gly Leu Thr Ala Ala Phe
1               5                   10                  15

Met Ser Ile Ser Met Phe Ser Ala Thr Ala Ser Ala
            20                  25

<210> SEQ ID NO 7
<211> LENGTH: 21
<212> TYPE: PRT
<213> ORGANISM: Escherichia coli

<400> SEQUENCE: 7

Met Lys Gln Ser Thr Ile Ala Leu Ala Leu Leu Pro Leu Leu Phe Thr
1               5                   10                  15

Pro Val Thr Lys Ala
            20

<210> SEQ ID NO 8
<211> LENGTH: 22
<212> TYPE: PRT
<213> ORGANISM: Escherichia coli

<400> SEQUENCE: 8

Met Met Lys Arg Asn Ile Leu Ala Val Ile Val Pro Ala Leu Leu Val
1               5                   10                  15

Ala Gly Thr Ala Asn Ala
            20

<210> SEQ ID NO 9
<211> LENGTH: 21
<212> TYPE: PRT
<213> ORGANISM: Escherichia coli

<400> SEQUENCE: 9

Met Lys Lys Ser Thr Leu Ala Leu Val Val Met Gly Ile Val Ala Ser
1               5                   10                  15

Ala Ser Val Gln Ala
            20

<210> SEQ ID NO 10
<211> LENGTH: 26
<212> TYPE: PRT
<213> ORGANISM: Escherichia coli

<400> SEQUENCE: 10

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 11
<211> LENGTH: 20
<212> TYPE: PRT
<213> ORGANISM: Escherichia coli

<400> SEQUENCE: 11

Met Lys Ala Thr Lys Leu Val Leu Gly Ala Val Ile Leu Gly Ser Thr
1               5                   10                  15

Leu Leu Ala Gly
            20
```

```
<210> SEQ ID NO 12
<211> LENGTH: 25
<212> TYPE: PRT
<213> ORGANISM: Escherichia coli

<400> SEQUENCE: 12

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 13
<211> LENGTH: 20
<212> TYPE: PRT
<213> ORGANISM: Escherichia coli

<400> SEQUENCE: 13

Met Arg Ala Lys Leu Leu Gly Ile Val Leu Thr Thr Pro Ile Ala Ile
1               5                   10                  15

Ser Ser Phe Ala
            20

<210> SEQ ID NO 14
<211> LENGTH: 21
<212> TYPE: PRT
<213> ORGANISM: Escherichia coli

<400> SEQUENCE: 14

Met Asn Lys Val Lys Cys Tyr Val Leu Phe Thr Ala Leu Leu Ser Ser
1               5                   10                  15

Leu Tyr Ala His Gly
            20
```